(12) United States Patent
Stuckler

(10) Patent No.: US 6,605,296 B1
(45) Date of Patent: Aug. 12, 2003

(54) NATURAL SUBSTANCES BASED AGENT

(75) Inventor: Franz Stuckler, Wolfsberg (AT)

(73) Assignee: Numico Research B.V., Wageningen (NL)

(*) Notice: Subject to any disclaimer, the term of this patent is extended or adjusted under 35 U.S.C. 154(b) by 0 days.

(21) Appl. No.: 09/581,475

(22) PCT Filed: Mar. 24, 1999

(86) PCT No.: PCT/AT99/00079

§ 371 (c)(1),
(2), (4) Date: Jun. 14, 2000

(87) PCT Pub. No.: WO99/48386

PCT Pub. Date: Sep. 30, 1999

(30) Foreign Application Priority Data

Mar. 24, 1998 (AT) ................................. 525/98

(51) Int. Cl.⁷ ........................... A61K 47/00; A61K 7/02
(52) U.S. Cl. ................... 424/439; 424/400; 424/441; 424/489; 424/442; 424/401
(58) Field of Search ................ 424/400, 439, 424/441, 489, 442, 401

(56) References Cited

U.S. PATENT DOCUMENTS

| | | | |
|---|---|---|---|
| 5,424,331 A | 6/1995 | Shlyankevich | |
| 5,569,458 A | 10/1996 | Greenberg | |
| 5,648,377 A | 7/1997 | Bombardelli et al. | |
| 5,702,714 A | 12/1997 | Goss | |
| 5,895,652 A | * 4/1999 | Giampapa | 424/195.17 |
| 6,099,854 A | * 8/2000 | Howard et al. | 424/440 |

FOREIGN PATENT DOCUMENTS

| | | |
|---|---|---|
| DE | 4120296 A1 | 3/1992 |
| EP | 0273407 A2 | 7/1988 |
| EP | 0712630 A2 | 5/1996 |
| GB | 2317561 A | 4/1998 |
| JP | 63000257 | 1/1988 |
| JP | 6070746 | 3/1994 |
| JP | 9077633 | 3/1997 |
| WO | WO9521542 | 8/1995 |
| WO | WO 9521542 | 8/1995 |
| WO | WO 9833494 | 8/1998 |
| WO | WO 9901148 | 1/1999 |

OTHER PUBLICATIONS

H.B. Fitch, "Antioxidants: Health Implications Still Debated," Inform, vol. 5, No. 3, 1994, pp. 242–243, 245–249, 251–252.

Marie–Annette Carbonneau et al., "Improvement in the Antioxidant Status of Plasma and Low–Density Lipoprotein in Subjects Receiving a Red Wine Phenolics Mixture," JAOCS, vol. 75, No. 2, (1998), pp. 235–240.

Database WPI, Section Ch, Week 9749, Derwent Publications Ltd., Longdon, GB; AN 97–527396 & CN 1 127 070 (HOU R), Jul. 24, 1996—Abstract.

Chemical Abstracts, vol. 127, No. 8, Aug. 25, 1997, Columbus, Ohio, S. Chanvitayapongs, "Amelioration of oxidative stress by antioxidants revseratrol in PC12 cells,".

* cited by examiner

Primary Examiner—James M. Spear
Assistant Examiner—Charesse Evans
(74) Attorney, Agent, or Firm—Young & Thompson

(57) ABSTRACT

A food supplement with advantageous physiological effects containing the following essential constituents in a support material (e.g. dairy products, margarine, fruit juice, plant juice, yeast, pectin or olive oil): lecithin, red wine extract and D-alpha-tocopherolacetate in amount ranging from 0.05 to 10.0 parts by weight.

37 Claims, No Drawings

NATURAL SUBSTANCES BASED AGENT

The invention relates to a preparation based on natural substances for internal and external use.

JP 6 070 746 A discloses a table vinegar which contains docosahexaenic acid and preferably 1 to 20% dried tuna fish extract. In addition, as claimed in JP 6 070 746 A, the table vinegar contains antioxidants such as tocopherol, lecithin, and/or catechin. The object of the composition of the table vinegar of JP 6 070 746 A is for the table vinegar and its products to have little fish smell and to have a good taste and aroma and good tactile sense. This moderates the irritation or the unpleasant fish smell. Medical applications and/or effects are not described.

EP 0 712 630 A2 relates to an oral composition for prevention of sun allergies. The composition is based on a carotinoid, a tocopherol, ascorbic acid, and selenium. Carotene and lycopene are used as the carotinoids. EP 0 712 630 A2 mentions the already known combination of antioxidants with vegetable oil as the adjuvant in the production of capsules for oral use. EP 0 712 630 A mentions lecithin solely as the adjuvant for capsule production. Medical applications and/or effects besides the action against sun allergies of the oral administration of the preparation of EP 0 712 630 A2 are not disclosed.

WO 95/21542 A1 discloses a beverage which is to be produced by the mixing of fruit juices and vegetable juices, oyster extract, glycyrrhizin, nonalcoholic red wine concentrate, wheat germ, soybean extract and seasonings. The beverage will contain provitamin A, vitamin A, vitamin E, vitamin C, trace elements, soluble fibers, flavonoids, glycyrrhizin, and taurine. It is also given in this citation that the red wine due to its flavonoid content has a preventative action against heart disease.

JP 630 00 257 A relates to a dried, sweet seed-corn product with 25 to 50% sugar, 1 to 25% soluble polysaccharides, 6 to 30% oil and 0.1 to 0.6% lecithin and tocopherol as the antioxidants. This is a product which can be taken orally and for which medical applications and/or effects are not validated.

U.S. Pat. No. 5,702,714 A relates to a composition for skin care which contains d-alpha-tocopherol oil, purcelline, (long chain and solid), and purcelline oil (a cetearyl octanoate) and pure silicic acid as the gelling agent for the oil, decyl oleate, squalane (brand name "Robane") which is a saturated, aliphatic hydrocarbon, wheat germ glyceride, proto-lan 8, consisting of phospholipids, lipo-polypeptides and lipo-aminic acids, polyoxypropylene esters and guaiazulene, a camomile extract. For the preparation of U.S. Pat. No. 5,702,714 A an improvement of the constitution of the skin by "rejuvenation" is validated. In conjunction with the component squalane it is pointed out that squalane is a saturated derivative of squalene and can be obtained by hydrogenation of natural, unsaturated squalene (see Martindale, The Extra Pharmacopoeia, 31st edition, 1996, page 1411).

JP 9 077 633 A discloses cosmetic compositions containing borage grass oil, with delta-tocopherol, ascorbic acid esters and/or lecithin. The cosmetic composition of JP 9 077 633 A is intended to improve the moist feeling on the skin and at the time of use have a good spreading property. The composition is intended for use in various areas, for example, foodstuffs, cosmetics, medicine, clothing.

As is known, food is absorbed in the human organism both in the gastrointestinal tract and also through the skin (internal and external). Thus, in external use bioactive substances, for example local rheumatism preparations or local varicose vein preparations, are absorbed into the human organisms.

According to the latest statistics on the causes of death in Germany, almost half of fatalities die from cardiac-circulatory diseases. Cancer is the second most frequent cause of death in Germany with almost one fourth. Cardiac-circulatory disease and cancer are thus responsible for almost three fourths of all causes of death. The numbers are similar in Austria. The urgency of effective prevention can be recognized from this.

The object of the invention is to make available a preparation of the initially mentioned type which has been prepared for example as a food supplement and which has advantageous physiological effects.

As claimed in the invention the preparation contains in a carrier substance as important components lecithin, red wine extract and D-alpha-tocopherol acetate, and optionally pectin in an amount of at least 0.50 parts by weight each.

Additional components in the food supplement can be the following: squalene, beta carotene, lycopene green tea extract, garlic extract, genistein, D-limonene, bisabolol (levomenol), leucocyanidol (pycnogenol), gingko biloba leaf extract, hawthorn extract, artichoke leaf extract, Blessed milkthistle fruit extract, ascorbic acid, B vitamins, olive leaf extract, escin, troxerutin, shitake mushroom extract (Lentinus edodes), frankincense extract (Boswellia), clawthorn extract, fish oil (salmon oil) concentrate, angurate extract and/or diosmine.

The B vitamins optionally contained in the preparation can be folic acid, vitamin B6, vitamin B12, nicotinamide, dexpanthenol, vitamin B1, vitamin B2, and/or biotin.

The preparation as claimed in the invention has beneficial effects on cardiac, circulatory and rheumatic conditions, acts preventively and strengthens the immune system against cancer.

It can be used for example preferably as a food supplement, as a biological, formula-free medication, body care preparation, healthy edible oil and healthy margarine.

The carrier substance can be a dairy product, margarine, fruit juice, olive oil, a vegetable juice, yeast, pectin or sorbite. The carrier substance can also be other substances such as cereals (for example, corn flakes) and other dry foods.

With respect to the components of the preparation as claimed in the invention, the following parts by weight always relating to the preparation as a whole; the following are listed:

Cold-pressed olive oil can form the carrier substance. The olive oil yields lipid-reducing, antiarteriosclerotic and anticancer effects. The high content of single unsaturated oleic acid which is present in cold-pressed olive oil is decisive for this purpose. The oleic acid significantly reduces the total cholesterol and the LDL cholesterol in the blood serum. Furthermore, the cold-pressed olive oil contains roughly 0.5% squalene which is an aliphatic triterpene, consisting of six isoprene units, Squalene has an antiinflammatory effect.

Lecithin is important to the extent that this component is a natural amphoteric emulsifier. Lecithin occurs in the cell membranes, in the lipoproteins of the blood plasma, in the liver, heart, kidneys, nerves, sperm and the bile, where it keeps the cholesterol together with bile acids in solution. Lecithin has a lipid-reducing effect when administered in a dose of a few grams. (See Hunnius, Pharmaceutical Dictionary [in German]. 8th edition, 1998, page 817).

Red wine extract (preferably 0.05 to 1.0 parts by weight) is important to the extent that it contains resveratrol as an important component. Resveratrol is 3,5,4'-trihydroxy-stilbene. Resveratrol is contained in larger amounts in the skin of blue wine grapes, in red wine and grape juice, in peanuts and mulberries. Resveratrol has been identified as an effective component in "Koyo-Kon" of folk medicine in China and Japan. Resveratrol is used to treat arteriosclerosis and acts against the tendency of the blood platelets to clump and reduces susceptibility to thrombosis. Red wine extract especially due to its content of resveratrol has protective effects against arteriosclerosis and cancer. Red wine with resveratrol protects the LDL particles in the blood much more strongly against oxidation than a comparable amount of likewise antioxidative vitamin E.

Free radicals and reactive oxygen compounds are involved in the formation of the most important common diseases such as cancer, arteriosclerosis and rheumatism. Conversely, antioxidants such as lecithin as a synergistic antioxidant, red wine extract, tocopherol, ascorbic acid, beta carotene, lycopene, squalene, green tea extract, garlic extract, genistein, leucocyanidol (pycnogenol), gingko biloba leaf extract, artichoke leaf extract, Blessed milkthistle fruit extract, which neutralize cell-damaging free radicals and aggressive oxygen compounds, are effective.

Tocopherol (vitamin E) (preferably 0.05 to 0.2 parts by weight) contains the diterpene phytol in the side chain (which is composed of four isoprene units). It occurs naturally in olive oil.

Squalene (preferably 0.05 to 0.5 parts by weight) occurs in plants, animals and man. Olive oil contains roughly 0.5 to 0.7%, human skin roughly 0.03%, but the liver oil of deep sea sharks contains 70 to 80% squalene.

Beta carotene (preferably 0.01 to 0.1 parts by weight) is a bicyclic tetraterpene. Beta carotene complements the action of other antioxidants such as that of tocopherol, and thus contributes to synergism of action. Therefore the two antioxidants, tocopherol and beta carotene, mainly in combination, play an important part in the prevention of arteriosclerosis and cancer. Beta carotene is the most frequently studied carotene with anticancer action. A regular, high supply of beta carotene has been associated with a low cancer risk in numerous studies, the level of supply influencing the beta carotene concentration in the blood. Low beta carotene concentrations in the serum are therefore considered a risk factor for cancer.

Lycopene (preferably 0.01 to 0.1 parts by weight) is an isomer of beta carotene, an aliphatic tetraterpene. It is the red color of tomatoes and paprika. Lycopene is an antioxidant and an outstanding radical trap which in certain tissues is much more effective than beta carotene. A high lycopene concentration in the blood has been associated with a low risk for rectal, pancreatic and gallbladder cancer.

Green tea extract (preferably 0.01 to 0.5 parts by weight) is obtained from green tea which has not been fermented and therefore contains more tannins, polyphenols. The polyphenols act as antioxidants. Green tea contains 7 to 25% catechin tannins and flavonoids. In laboratory tests the antioxidative effect of green tea catechins has been found to be twenty times as great as that of vitamin E. Green tea benefits blood cholesterol and blood pressure values. The anticancer effect of green tea has been confirmed in animal tests.

Garlic extract (preferably 0.01 to 0.5 parts by weight) can be obtained using olive oil in natural and unaltered form: For example, 6 to 8 fresh peeled garlic bulbs are allowed to steep in 500 ml olive oil for 2 to 3 weeks and the olive oil is then poured off. In the oil macerate obtained in this way the active garlic preparations are carefully obtained. The sulfur-containing vegetable substances of garlic have a protective effect against arteriosclerosis and also anticancer effects. They improve the flow properties of the blood, reduce high blood pressure, inhibit blood coagulation and sticking of blood platelets, and inhibit oxidation of LDL cholesterol as an antioxidant.

Genistein (preferably 0.01 to 0.2 parts by weight) is a phyto estrogen and is considered among the isoflavonoids (5,7,4'-trihydroxy isoflavone). Genistein occurs in soybeans, in the blossoms of the common woadwaxen (Genista tinctoria, therefore the name) and in the fruit of the Japanese pagoda tree (Sophora japonica).

D-limonene (preferably 0.01 to 0.2 parts by weight) is a cyclic monoterpene which is composed of two isoprene units. It occurs in many essential oils, such as citrus, orange peel, bergamot, caraway, dill and turpentine oil. D-limonene has an anticancer action.

Bisabolol (levomenol) (preferably 0.01 to 0.1 parts by weight) is a sesquiterpene alcohol which consists of three isoprene units. It occurs in camomile oil and acts as an anti-inflammatory, promotes granulation, is a spasmolytic and disinfectant. To date it has been used mainly as a varicose vein preparation, for wound treatment and in skin diseases.

Leucocyanidol (pycnogenol) (preferably 0.01 to 0.2 parts by weight) is a natural substances from the group of catechins and occurs widely in the plant kingdom, for example in the hawthorn. It is used as to improve venous tone, for example in varicose veins and as a vasoprotective preparation. Leucocyanidol acts as an antioxidant. It improves the stabilizing action of vitamin C on connective tissue of the blood vessel walls.

Gingko biloba leaf extract (preferably 0.01 to 0.1 parts by weight). The gingko tree is the oldest tree on earth and therefore a robust plant which is rich in vital substances.

For thousands of years the gingko has been used as a medicinal plant in China. The leaves contain bioactive plant substances: flavonol glycosides, bisflavonoids (for example ginkgetin), ginkgolides, bilobalide (terpene lactones) and procyanidines. As an antioxidative radical trap gingko biloba leaf extract prevents lipid peroxidation by neutralization of toxic oxygen radicals. It improves the flow properties of the blood via reduction of thrombocyte and erythrocyte aggregation and via reduction of blood viscosity. It promotes oxygen absorption and use in the tissue. The peripheral and cerebral blood circulation of arterial vessels is improved. Therefore it is effective in conditions which occur as a result of arteriosclerotic changes of these vessels. In animal tests on rats gingko biloba leaf extract caused not only an improvement of memory and faster learning, but surprisingly also a significant prolongation of longevity.

Hawthorn extract (Crataegus oxyacantha, preferably 0.01 to 0.3 parts by weight). This extract of the leaves, blossoms and fruits of the hawthorn contains bioactive constituents: oligomer procyanidines (for example, pycnogenol), epicatechin, catechins, flavonoids (for example, hyperoside, a quercetin galactoside, vitexin with apigenin, a trihydroxyflavone), crataegussic acid (tripertenic acids), phenol carboxylic acids (caffeic acid, chlorogenic acid). Hawthorn extract is an universal cardiac preparation, both with preventative and also with healing action in circulatory problems of the cardiac vessels and heart muscle. Furthermore it has a improves rhythm of the heart and circulation. In addition, the tolerance of the heart muscle to oxygen shortage is increased. Finally, it increases heart performance and reduces peripheral vessel resistance.

Artichoke leaf extract (Cynara scolymus, preferably 0.02 to 0.3 parts by weight). The artichoke is a Mediterranean vegetable. The leaves contain bioactive plant substances: the bitterns cynaropicrin (sesquiterpene lactone) and cynarin (quinic acid dicaffeic acid ester) and caffeic acid and chlorogenic acid (quinic acid-caffeic acid ester), luteolin (tetrahydroxy flavone) and its glycosides cynaroside and scolymoside. Artichoke leaf extract reduces the cholesterol level in the blood by biological means.

Blessed milkthistle fruit extract (Silybum marianum, preferably 0.01 to 0.3 parts by weight). Blessed milkthistle, like the artichoke, is a composite flower. The fruits contain the bioactive plant complex silymarin which consists of three isomer flavonolignans, silibinin, silidianin and silicristin. Blessed milkthistle fruit extract increases the regeneration capacity of the liver.

B vitamins (folic acid, vitamin B6 and vitamin B12). Homocysteine, a protein decomposition product, promotes deposition of blood fats such as cholesterol in the blood vessels. The three B vitamins jointly provide for balanced metabolism and reduce homocysteine in the blood. Homocysteine is considered a risk factor for arteriosclerosis.

B-vitamins are contained preferably in the following amounts: Folic acid: 0.001 to 0.01 parts by weight, vitamin B6: 0.002 to 0.02 parts by weight, vitamin B12: 0.000 001 to 0.000 01 parts by weight, (=1 to 10 micrograms) nicotinamide: 0.005 to 0.05 parts by weight, dexpanthenol: 0.002 to 0.02 parts by weight, vitamin B1: 0.002 to 0.01 parts by weight, vitamin B2: 0.002 to 0.01 parts by weight, biotin: 0.0001 to 0.001 parts by weight).

Ascorbic acid (preferably 0.02 to 0.2 parts by weight) can advantageously be microencapsulated. Vitamin C is found in all living cells. It is essential for the stability of the blood vessels and the cardiac muscle tissue. Vitamin C is the "protection factor" of the arteries since it stabilizes the arterial walls.

Clawthorn root extract (Uncaria tomentosa, preferably 0.01 to 0.2 parts by weight). In Indian folk medicine Uncaria tomentosa (clawthorn, family Rubiaceae, genus Gentianales) has been used therapeutically for a long time. The bioactive plant substances of the roots are oxindol alkaloids, such as pteropodine. It strengthens the immune system as an outstanding immune stimulant.

Shitake mushroom extract (Lentinus edodes, preferably 0.01 to 0.5 parts by weight):

The East Asian Shitake mushroom is cultivated in the Far East in large amounts. In Europe it is becoming more and more popular. The mushroom imparts to food a pleasantly spicy taste. According to many scientific studies in Japanese clinics the mushroom has a three-fold healing and protective effect: antiviral, antithrombotic and cytotoxic. This means that it reduces cholesterol, prevents formation of thromboses by clumping of blood platelets, and suppresses virus infections. In addition, in many studies on humans the mushroom has inhibited and suppressed cancer cell growth. One of its constituents, lentinan, is a polysaccharide, (1,3)-beta-D-glucan, which has two branch points per 5 glucose molecules and has a molecular weight of roughly 1 million. Lentinan is antibacterial and stimulates the non-specific immune system. Lentinan is used in Japan together with chemotherapy to treat tumors. It improves the function of macrophages and T-lymphocytes. In particular lentinan stimulates the formation of interluekin-1, a tumor-killing substance, and increases the cell-killing action of the macrophages. According to more recent research lentinan is said prevent the formation of metastases in lung cancer.

Frankincense extract (Boswellia, preferably 0.1 to 0.2 parts by weight). The gum resin of the frankincense tree (Boswellia bhaw-dajiana) contains 50–70% alcohol-soluble resins. They consist one half of boswellic cad, a triterpene carboxylic acid (melting point roughly 230° C.) and similar compounds such as keto boswellic acid and 6–8% bassorin, a polysaccharide which is not soluble in water, but which can swell greatly (molecular weight more than 100,000). The boswellic acid has a beneficial effect in rheumatic conditions and polyarthritis.

Furthermore, frankincense extract is used in inflammatory brain swelling and in the treatment of brain tumors. A clear cancer cell-killing effect of frankincense extract has been demonstrated.

Olive leaf extract (preferably 0.1 to 0.2 parts by weight). Olive leaves contain bioactive plant substances which reduce blood pressure. Olive leaves are used in the form of a decoction, a tincture, or dry extract as a preparation which reduces blood pressure. The active preparations are bitters with a blood pressure-reducing action which as oleuropein, an ester glycoside with secoiridoid base structure which is soluble in water. The secoiridoids are found mainly in olive tree plants (Oleaceae) and gentian plants (Gentianaceae). Olive leaf extract is used against high blood pressure, angina pectoris, to prevent general blood vessel sclerosis and to increase urine excretion by the kidneys. Oleuropein acts to an antispasmodic and reduces both the systolic and also the diastolic blood pressure.

Anguarate extract (Angurate, Mentzelia cordifolia Dombey, preferably 0.1 to 0.5 parts by weight). The extract contains as bioactive plant substances flavonoids, such as quercetin and camphor oil, furthermore bitters and sitosterin (phytosterin). The tea is used and as antiinflammatory and stomach and intestinal antispasmodic.

Escin (preferably 0.01 to 0.1 parts by weight). It is a horse chestnut extract. It is a mixture of esterified triterpene saponins composed of 30 pure substances. Escin acts as an antiinflammatory and prevents formation of edemas, is a diuretic and increases capillary permeability. It is therefore used in treatment of edemas and as a treatment for varicose veins.

Troxerutin (preferably 0.02 to 0.2 parts by weight). It is a water-soluble rutin with 3 hydroxy-ethyl groups. Troxerutin is used for venous and capillary insufficiency and in retinal damage.

Pectin (preferably 1.0 to 3.0 parts by weight). Pectin consists essentially of galactonuric acid units linked in a glycoside bond. The number of these units is several hundred. Pectins are contained in almost all plant tissues capable of growth. Pectin gels in an aqueous solution. Pectin is used for treatment of diarrhea, gastroenteritis, gastrointestinal ulcers, and for wound treatment. In the food industry pectin is used as a stabilizer, emulsifier and thickener. Pectin outstandingly detoxifies the intestine and acts preventively against arteriosclerosis and cardiac infarction. In higher doses (roughly 15 g daily) it reduces the cholesterol level.

Diosmin (preferably 0.03 to 0.3 parts by weight). It is 5,7,3'-trihydroxy-4'-methoxy-flavone-7-rhamnoglucoside (diosmetin-7-rutinoside). Diosmin is used in chronic venous complaints and general venous insufficiency.

Fish oil (preferably 0.1 to 0.5 parts by weight). For example a salmon concentrate, enriched to roughly 30% vital omega-3-fatty acids, such as eicosapentaenic acid (EPA with 20 C atoms and 5 double bonds) and docosahexaenic acid (DHA, with 22 C 30 atoms and 6 double bonds). The omega-3-fatty acids especially reduce the triglyceride level and reduce thrombocyte aggregation. They dilate the blood vessels, reduce blood pressure, improve blood flow properties and are antiinflammatory.

In the following, examples for the preparation as claimed in the invention are given:

EXAMPLE 1

| Parts by weight/component | Preferred range (parts by weight) |
|---|---|
| 95.00 olive oil (as the carrier) | 99.14 to 85.8 |
| 3.00 lecithin (for example, microencapsulated) | 0.5 to 10.0 |
| 0.5 red wine extract (dry) | 0.1 to 1.0 |
| 0.2 D-alpha-tocopherol acetate (for example, microencapsulated) | 0.05 to 1.0<br>0.05 to 0.5 |

In addition, the preparation can contain one or more of the following components in the indicated amounts:

| Parts by weight/component | Preferred range (parts by weight): |
|---|---|
| 0.2 ascorbic acid (for example, microencapsulated) | 0.1 to 1.00 |
| 0.1 luecocyanidol (pycnogenol) | 0.1 to 0.2 |
| 0.5 beta-carotene | 0.01 to 0.1 |
| 0.05 lycopene | 0.01 to 0.1 |
| 0.05 nicotinamide | 0.01 to 0.1 |
| 0.1 green tea extract | 0.01 to 0.2 |
| 0.5 garlic extract | 0.01 to 0.5 |
| 0.05 genistein | 0.01 to 0.1 |
| 0.05 D-limonene | 0.01 to 0.1 |
| 0.05 bisabolol (levomenol) | 0.01 to 0.1 |
| 0.05 gingko biloba leaf extract | 0.01 to 0.1 |
| 0.05 frankincense extract | 0.01 to 0.1 |

EXAMPLE 2

A food supplement with advantageous physiological properties contains margarine as the carrier and the following as the important components:

|  | (Parts by weight) |
|---|---|
| olive oil (in the form of margarine as the carrier substance) | 60.0 to 75.0 |
| lecithin (for example, microencapsulated) | 1.0 to 5.0 |
| red wine extract (dry) | 0.1 to 1.- |
| D-alpha-tocopherol acetate (for example, microencapsulated) | 0.05 to 0.4 |

In addition, the preparation can contain one or more of the following components in the indicated amounts:

| beta carotene | 0.01 to 0.05 |
|---|---|
| lycopene | 0.01 to 0.05 |
| squalene | 0.01 to 0.05 |
| green tea extract | 0.1 to 0.5 |
| garlic extract | 0.1 to 0.5 |
| genistein | 0.01 to 0.2 |
| D-limonene | 0.01 to 0.2 |
| bisabolol (levomenol) | 0.01 to 0.1 |
| leucocyanidol (pycnogenol) | 0.01 to 0.2 |
| ascorbic acid (for example, microencapsulated) | 0.1 to 0.3 |
| nicotinamide | 0.01 to 0.1 |
| pectin | 0.5 to 1.- |
| olive leaf extract | 0.01 to 0.2 |
| artichoke leaf extract | 0.02 to 0.3 |
| Blessed milkthistle fruit extract | 0.01 to 0.3 |
| gingko biloba leaf extract | 0.01 to 0.1 |
| hawthorn extract | 0.01 to 0.3 |
| escin | 0.01 to 0.1 |
| troxerutin | 0.01 to 0.1 |
| shitake mushroom extract (Lentinus edodes) | 0.01 to 0.5 |
| frankincense extract (Boswellia) | 0.01 to 0.2 |
| clawthorn root extract (Uncaria tomentosa) | 0.01 to 0.2 |
| diosmin | 0.01 to 0.3 |
| anguarate extract | 0.01 to 0.5 |
| water and food adjuvants | 38.35 to 14.40 |
| vitamin D | 2.5 micrograms |

Margarine is produced using a conventional method for a water-in-oil emulsion. The fat component is solely cold-pressed olive oil with the addition of skimmed milk. Emulsifiers are lecithin and for example casein, a phosphoprotein, which like lecithin is an ampholyte, and monodiglyceride. Preservatives and buttery flavor, like milk and diacetyl and the dye beta carotene, can be added.

The margarine is not solidified and not converted and is therefore a daily contribution to healthy nutrition. It does not contain any trans-fatty acids.

EXAMPLE 3

A food additive with advantageous physiological effects contains yogurt as the carrier:

| Component | Parts by weight |
|---|---|
| yogurt | 91.41 to 84.5 |
| fruit preparation | 7.0 to 10.0 |
| lecithin (for example, microencapsulated) | 0.1 to 1.0 |
| red wine extract | 0.05 to 0.1 |
| D-alpha-tocopherol acetate (for example, microencapsulated) | 0.05 to 0.1 |
| pectin | 1.0 to 2.0 |

In addition the preparation can contain one or more of the following components in the indicated quantities:

| B-vitamins: | Parts by weight |
|---|---|
| folic acid (for example, microencapsulated) | 0.0001 to 0.001 |
| vitamin B6 (for example, microencapsulated) | 0.001 to 0.005 |
| vitamin B12 (for example, microencapsulated) | $\mu$g 1 to 3 |
| nicotinamide | 0.005 to 0.01 |
| dexpanthenol | 0.002 to 0.005 |
| vitamin B1 | 0.001 to 0.003 |
| vitamin B2 | 0.001 to 0.003 |
| biotin | 0.0001 to 0.0002 |
| ascorbic acid (for example, microencapsulated) | 0.02 to 0.1 |
| squalene | 0.01 to 0.1 |
| beta carotene | 0.005 to 0.01 |
| lycopene | 0.005 to 0.01 |
| genistein | 0.01 to 0.1 |
| green tea extract | 0.01 to 0.2 |
| garlic extract | 0.01 to 0.2 |
| olive leaf extract | 0.01 to 0.1 |
| D-limonene | 0.01 to 0.1 |
| bisabolol (levomenol) | 0.01 to 0.05 |
| leucocyanidol (pycnogenol) | 0.01 to 0.05 |

-continued

| B-vitamins: | Parts by weight |
|---|---|
| artichoke leaf extract | 0.02 to 0.1 |
| Blessed milkthistle extract | 0.02 to 0.1 |
| anguarate extract | 0.01 to 0.1 |
| (extract of angurate, Peru) | |
| gingko biloba leaf extract | 0.01 to 0.05 |
| hawthorn extract | 0.01 to 0.05 |
| escin | 0.01 to 0.05 |
| troxerutin | 0.01 to 0.1 |
| diosmin | 0.05 to 0.1 |
| shitake mushroom extract | 0.01 to 0.1 |
| (lentinus edodes) | |
| frankincense extract (Boswellia) | 0.01 to 0.1 |
| Clawthorn root extract | 0.01 to 0.1 |
| (Uncaria tomentosa) | |
| Salmon oil concentrate | 0.01 to 0.3 |

EXAMPLE 4

Chewable Tablets or Granulate:

A chewable tablet or a granulate with advantageous physiological effects can be composed of the following, for example:

Carrier substance: medicinal yeast, pectin, sorbite, additionally corn flakes or other dry food, and as the important components

| Parts by weight/component | Preferred range (parts by weight) |
|---|---|
| 3.0 pectin (as the carrier substance) | 1.0 to 3.0 |
| 1.0 lecithin | 1.0 to 10.0 |
| 0.5 red wine extract | 0.1 to 1.0 |
| 0.2 D-alpha-tocopherol acetate | 0.05 to 0.5 |

The other components are the same as in example 2 (margarine) and in the same composition.

A skin care preparation for external use can have the following composition for example:

Olive oil as the dermally-bioactive carrier substance contains the following as important components:

lecithin (for example, microencapsulated), red wine extract,

D-alpha-tocopherol acetate (for example, microencapsulated)

In addition, the preparation can contain one or more of the components listed below:

squalene, halibut liver oil, aloe vera, lycopene, beta carotene, bisabolol (levomenol), D-limonene, ascorbic acid (for example, microencapsulated), leucocyanidol (pycnogenol), allantoin, dexpanthenol, nicotinamide, biotin, gingko biloba leaf extract, green tea extract, marigold extract (Calendula officinalis, with triterpene saponins, carotinoids, flavonoids), berberine (European barberry, Berberis vulgaris, with isoquinoline alkaloid), frankincense extract (Boswellia, with boswellic acid, a triterpene carboxylic acid), escin (triterpene-saponin mixture of horse chestnut), hamamelis extract (oligomer proanthocyanidins), troxerutin (flavonoid from buckwheat, for example), diosmin (flavonoid from hyssop, for example), heparin sodium, pectin and water).

Fruit juice- or vegetable juice-based preparations can contain the following components as claimed in the invention:

A preparation prepared as a fruit juice or vegetable juice or tomato product or a mixture thereof can have the following composition, for example: As the carrier substance a fruit juice, for example: red grape juice, apple juice, blueberry juice, black currant juice, rose-hip juice, sea buckthorn juice, barberry juice, quince juice, grapefruit juice, orange juice, apricot juice, papaya juice, maracuya juice, banana juice, kiwi juice, mango juice, raspberry juice or raspberry syrup.

Alternatively a vegetable juice is contained as a carrier substance, for example: soy milk, broccoli juice, artichoke juice, hawthorn juice, gingko biloba juice, Blessed milkthistle juice, red beet juice, black radish juice, garlic juice, leek juice, carrot juice, celery juice, stinging nettle juice, dandelion juice, bone juice, birch juice or horsetail juice.

The tomato product contains as the carrier substance tomato juice or tomato pulp or tomato ketchup.

These fruit or vegetable juices can also be used as a concentrate or dry extract or as biologically high quality base and carrier substances in this form.

The fruit juice or the vegetable juice or the tomato product or a mixture thereof, contains the following as essential components:

lecithin (with or without solubilizers or microencapsulated), red wine extract (with its optimum content of resveratrol), D-alpha-tocopherol acetate (for example, microencapsulated).

In addition, the preparation can contain one or more of the following components:

Pectin, fructose, ascorbic acid (for example, microencapsulated), B vitamins such as folic acid (for example, microencapsulated), vitamin B6 (for example, microencapsulated), vitamin B12 (for example, microencapsulated), nicotinamide, dexpanthenol, vitamin B1, vitamin B2, biotin. Furthermore squalene, lycopene, beta carotene, leucocyanidol (pycnogenol), genistein, green tree extract, artichoke leaf extract, Blessed milkthistle fruit extract, gingko biloba leaf extract, hawthorn extract, olive leaf extract, escin, troxerutin, anguarate extract or diosmin.

A tomato product such as tomato juice or tomato pulp or tomato ketchup can additionally contain one or more of the following components, besides those already indicated:

Olive oil, garlic powder or garlic concentrate, or garlic extract or garlic macerate with water or oil such as olive oil, or essential garlic oil or another garlic product.

Furthermore, salmon oil concentrate, D-limonene, or bisabolol (levomenol), shitake mushroom (Lentinus edodes) as a powder or extract with the bioactive plant substance lentinan, clawthorn root extract (Uncaria tomentosa) with the bioactive plant substance pteropodin, an oxindol alkaloid, frankincense extract (Boswellia) with the bioactive plant substance boswellic acid, a tripertene carboxylic acid.

EXAMPLE 5

Fruit juice- or vegetable juice-based preparation

As the carrier substance: red grape juice, or black currant juice, or red beet juice or tomato juice, or one of the indicated fruit or vegetable juices.

| Parts by weight/component | Preferred range (Parts by weight) |
|---|---|
| Red grape juice (as the carrier substance ad 100) | |
| 5.0 lecithin | 1.0 to 10.0 |
| 0.5 red wine extract | 0.1 to 1.0 |
| 0.2 D-alpha-tocopherol acetate | 0.05 to 0.4 |

In addition, the preparation can contain one or more of the following components in the indicated amount:

| | |
|---|---|
| 0.05 beta carotene | 0.01 to 0.1 |
| 0.05 lycopene | 0.01 to 0.1 |
| 0.05 squalene | 0.01 to 0.1 |
| 0.2 ascorbic acid (for example, microencapsulated) | 0.1 to 0.5 |
| 0.2 leucocyanidol (pycnogenol) | 0.1 to 0.3 |
| 0.3 artichoke leaf extract | 0.1 to 0.3 |
| 0.3 garlic extract | 0.1 to 0.5 |
| 0.05 gingko biloba extract | 0.01 to 0.1 |
| 0.2 hawthorn extract | 0.1 to 0.3 |
| 0.1 olive leaf extract | 0.1 to 0.2 |
| 0.2 green tea extract | 0.1 to 0.5 |
| 0.1 genistein | 0.01 to 0.2 |
| 0.1 frankincense extract | 0.01 to 0.2 |
| 0.1 D-limonene | 0.01 to 0.2 |
| 0.1 escin | 0.01 to 0.2 |
| 0.1 troxerutin | 0.01 to 0.2 |
| 0.1 diosmin | 0.01 to 0.2 |
| 0.1 bisabolol | 0.01 to 0.2 |
| 0.1 clawthorn root extract | 0.01 to 0.2 |
| 0.1 shitake mushroom extract | 0.01 to 0.2 |
| 0.3 salmon oil concentrate | 0.1 to 0.5 |
| B-vitamins: | |
| 0.003 folic acid | 0.001 to 0.01 |
| 0.02 vitamin B6 | 0.002 to 0.02 |
| 0.000 003 vitamin B12 | $\mu g$ 1 to 3 |
| 0.05 nicotinamide | 0.01 to 0.05 |
| 0.01 dexpanthenol | 0.01 to 0.02 |
| 0.01 vitamin B1 | 0.002 to 0.01 |
| 0.01 vitamin B2 | 0.002 to 0.01 |
| 0.001 biotin | 0.0001 to 0.001 |

Alcohol content: 15%

The food supplement without olive oil can wth its bioactive components be mixed with dairy products such as for example yogurt, kefir, kumiss, milk and whey, with or without fruit preparations. In this way biological healthy dairy products in the sense of orthomolecular medicine are obtained. Furthermore, the food supplement without olive oil can be mixed for example with watered fruit juices, for example red grape juice. This yields bioactive fruit beverages in the sense of orthomolecular medicine, which uses pharmaceuticals which also occur in natural food and are therefore not foreign to our body (according to R. J. Williams, pharmaceuticals of type 2).

With the preparation as claimed in the invention among others the following advantageous physiological effects can be achieved:

Help in and prevention of cardiac and circulatory conditions.

Help and relief as well as prevention of cancers.

Help and relief in rheumatic conditions.

lipid-reducing action.

Antiarteriosclerotic action.

Strengthening of the immune system.

Action against premature aging processes, such as for example skin aging and/or organ aging (for example heart, lungs, blood vessels)

What is claimed is:

1. A preparation based on natural substances for internal and external use, characterized in that a carrier substance contains lecithin, red wine extract containing resveratrol, and tocopherol (vitamin E), in an amount of at least 0.05 parts by weight each, fish oil in an amount of 0.1 to 0.5 part by weight, folic acid in an amount of at least 0.0001 part by weight, vitamin B6 in an amount of at least 0.001 part by weight, and vitamin B12 in an amount of at least 0.000001 part by weight.

2. Preparation as claimed in claim 1, wherein the carrier substance is selected from the group consisting of a dairy product, margarine, a vegetable or fruit juice, olive oil, yeast, pectin, sorbite, and a mixture thereof.

3. Preparation as claimed in claim 1, wherein the lecithin, red wine extract and tocopherol are present in amounts of 0.05 to 10.0 parts by weight each.

4. Preparation as claimed in claim 1, wherein said preparation contains 0.5 to 10.0 parts by weight lecithin.

5. Preparation as claimed in claim 1, wherein said preparation contains 0.1 to 1.0 parts by weight red wine extract (dry).

6. Preparation as claimed in claim 1, wherein said preparation contains 0.05 to 0.5 tocopherol.

7. Preparation as claimed in claim 1, wherein it contains in amounts of 0.01 to 1.0 parts by weight each of squalene, beta carotene, lycopene, green tea extract, garlic extract, genistein, D-limonene, bisabolol (levomenol), leucocyanidol (pycnogenol), ascorbic acid, gingko biloba leaf extract, hawthorn extract, artichoke leaf extract, Blessed milk thistle fruit extract, olive leaf extract, escin, troxerutin, shitake mushroom extract (Lentinus edodes), frankincense extract (Boswellia), anguarate extract, diosmin, fish oil and clawthorn root extract, and B vitamins in an amount of at least 0.0001 parts by weight, vitamin B6 in an amount of at least 0.001 parts by weight, and vitamin B12 in an amount of at least 0.000001 parts by weight.

8. Preparation as claimed in claim 1, wherein said preparation contains 0.1 to 0.5 parts by weight squalene.

9. Preparation as claimed in claim 1, wherein said preparation contains 0.01 to 0.1 parts by weight beta carotene.

10. Preparation as claimed in claim 1, wherein said preparation contains 0.01 to 0.1 parts by weight lycopene.

11. Preparation as claimed in claim 1, wherein said preparation contains 0.01 to 0.3 parts by weight green tea extract.

12. Preparation as claimed in claim 1, wherein said preparation contains 0.01 to 0.2 parts by weight genistein.

13. Preparation as claimed in claim 1, wherein said preparation contains 0.01 to 0.2 parts by weight D-limonene.

14. Preparation as claimed in claim 1, wherein said preparation contains 0.01 to 0.1 parts by weight bisabolol (levomenol).

15. Preparation as claimed in claim 1, wherein said preparation contains 0.01 to 0.2 parts by weight leucocyandiol (pycnogenol).

16. Preparation as claimed in claim 1, wherein said preparation contains 0.01 to 0.1 parts by weight gingko biloba leaf extract.

17. Preparation as claimed in claim 1, wherein said preparation contains 0.01 to 0.3 parts by weight hawthorn extract.

18. Preparation as claimed in claim 1, wherein said preparation contains 0.01 to 0.3 parts by weight artichoke leaf extract.

19. Preparation as claimed in claim 1, wherein said preparation contains 0.01 to 0.3 parts by weight Blessed milk thistle fruit extract.

20. Preparation as claimed in claim 1, wherein said preparation contains 0.01 to 0.2 parts by weight olive leaf extract.

21. Preparation as claimed in claim 1, wherein said preparation contains 0.01 to 0.1 parts by weight escin.

22. Preparation as claimed in claim 1, wherein said preparation contains 0.01 to 0.1 parts by weight troxerutin.

23. Preparation as claimed in claim 1, wherein said preparation contains 0.01 to 0.5 parts by weight shitake mushroom extract.

24. Preparation as claimed in claim 1, wherein said preparation contains 0.01 to 0.2 parts by weight frankincense extract (Boswellia).

25. Preparation as claimed in claim 1, wherein said preparation contains 0.01 to 0.2 parts by weight clawthorn root extract (Uncaria tomentosa).

26. Preparation as claimed in claim 1, wherein said preparation contains 0.001 to 0.01 parts by weight folic acid, 0.001 to 0.01 parts by weight vitamin B6, 0.005 to 0.01 parts by weight nicotinamide, 0.002 to 0.01 parts by weight dexpanthenol, 0.001 to 0.01 parts by weight vitamin B1, 0.001 to 0.01 parts by weight vitamin B2, 0.0001 to 0.001 parts by weight biotin, and 0.000001 to 0.00001 parts by weight vitamin B12.

27. Preparation as claimed in claim 1, in a carrier substance which is a fruit juice.

28. Preparation as claimed in claim 1, in a carrier substance which is a vegetable juice.

29. Preparation as claimed in claim 1, carrier substance is yogurt, kefir, kumiss, milk and whey.

30. Preparation as claimed in claim 1, wherein said preparation is prepared as a chewable tablet or as a granulate and as a carrier substance contains a member selected from the group consisting of yeast, pectin, sorbite and a mixture thereof.

31. Preparation as claimed in claim 1, wherein said preparation is prepared as corn flakes and contains corn as a carrier substance.

32. Preparation as claimed in claim 1, wherein said preparation is prepared as tomato pulp or as tomato ketchup and contains tomatoes as a carrier substance.

33. Preparation as claimed in claim 1, wherein said preparation is prepared as a skin care preparation which can be externally applied and contains olive oil as a carrier substance.

34. Preparation as claimed in claim 1, wherein it contains 0.5 to 3.0 parts by weight pectin.

35. Preparation as claimed in claim 1, wherein it contains 0.01 to 0.5 parts by weight garlic extract.

36. Preparation as claimed in claim 7, wherein it contains 0.01 to 0.3 parts by weight diosmin.

37. Preparation as claimed in claim 7, wherein it contains 0.01 to 0.5 parts by weight anguarate extract.

* * * * *